(12) United States Patent
Lootz

(10) Patent No.: US 6,565,598 B1
(45) Date of Patent: May 20, 2003

(54) STENT WITH A CLOSED STRUCTURE

(75) Inventor: Daniel Lootz, Rostock (DE)

(73) Assignee: Biotronik Mess -und Therapiegeraete GmbH & Co. Ingenieurbuero Berlin, Berlin (DE)

(*) Notice: Subject to any disclaimer, the term of this patent is extended or adjusted under 35 U.S.C. 154(b) by 81 days.

(21) Appl. No.: 09/695,725

(22) Filed: Oct. 24, 2000

(30) Foreign Application Priority Data

Oct. 26, 1999 (DE) .......................................... 199 51 607

(51) Int. Cl.⁷ ................................................. A61F 2/24
(52) U.S. Cl. ...................................................... 623/1.15
(58) Field of Search ................................. 623/1.1, 1.16, 623/1.12, 1.15, 1.17, 1.2, 1.32; 606/198, 195

(56) References Cited

U.S. PATENT DOCUMENTS

| | | |
|---|---|---|
| 4,655,771 A | 4/1987 | Wallsten |
| 4,733,665 A | 3/1988 | Palmaz |
| 4,739,762 A | 4/1988 | Palmaz |
| 4,776,337 A | 10/1988 | Palmaz |
| 4,954,126 A | 9/1990 | Wallsten |
| 5,061,275 A | 10/1991 | Wallsten |
| 5,102,417 A | 4/1992 | Palmaz |
| 5,104,404 A | 4/1992 | Wolff |
| 5,195,984 A | 3/1993 | Schatz |
| 5,449,373 A | 9/1995 | Pinchasik |
| 5,562,697 A | 10/1996 | Christiansen |
| 5,800,508 A | 9/1998 | Goicoechea |
| 5,968,093 A | 10/1999 | Kranz |
| 5,972,018 A * | 10/1999 | Israel et al. ................. 606/198 |
| 6,051,001 A | 4/2000 | Borghi |
| 6,066,169 A * | 5/2000 | McGuinness ............... 623/1.16 |
| 6,183,506 B1 * | 2/2001 | Penn et al. .................. 623/1.15 |
| 6,193,744 B1 * | 2/2001 | Ehr et al. .................... 623/1.15 |

FOREIGN PATENT DOCUMENTS

| | | |
|---|---|---|
| DE | 196 53 721 A1 | 4/1998 |
| DE | 196 53 718 C2 | 6/1999 |
| EP | 0 847 733 A1 | 6/1998 |
| EP | 0 847 734 A2 | 6/1998 |
| WO | WO 97/32543 A1 | 9/1997 |
| WO | WO 97/32546 A1 | 9/1997 |

* cited by examiner

*Primary Examiner*—Corrine McDermott
*Assistant Examiner*—William H Matthews
(74) *Attorney, Agent, or Firm*—Hahn Loeser + Parks LLP; Stephen L. Grant

(57) ABSTRACT

A stent has a tubular portion which has openings that are of a substantially V-shaped configuration.

15 Claims, 1 Drawing Sheet

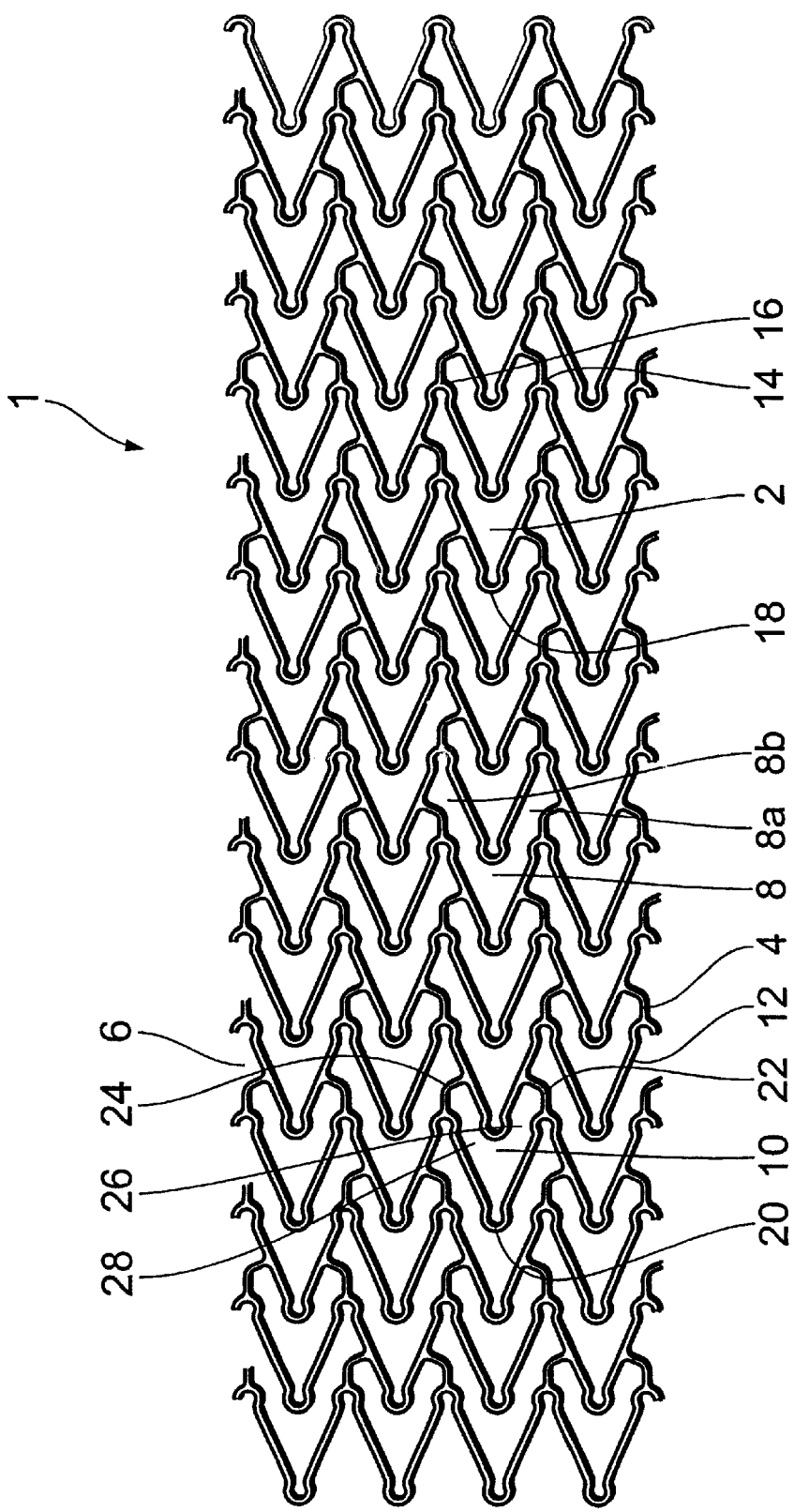

STENT WITH A CLOSED STRUCTURE

BACKGROUND OF THE ART

Stents of that kind are known from the state of the art in many different forms. Those stents are used inter alia in connection with percutaneous transluminal angioplasty (PCTA, Percutaneous Transluminal Balloon Angioplasty), in vascular surgery of the heart. Stents however can also serve to dilate other openings in the body or to keep such openings in a dilated condition. That medical procedure is initially preceded by determining the location of the constriction in a coronary blood vessel. A so-called angioplasty balloon is then moved in the artery which has the constriction, the so-called stenosis, to the location of the stenosis where it is inflated. Due to the radially outwardly directed force of the inflated balloon the constriction is dilated and in the optimum case the original passage cross-section of the previously constricted artery is restored. Besides successful dilation of the vessel however side-effects can also occur, which include local splits in the artery, disintegration effects and projections of plate portions and flakes into the lumen of the artery so that, in spite of the dilation effect, blockage of the vessel can still occur. In addition it is possible that a stenosis can recur due to the vessel wall elastically springing back and/or due to the growth of the intima of the vessel. Statistically, that occurs within six months in the case of over 30% of the patients who were treated with PCTA.

In order now immediately after dilation of the blood vessel to ensure a relatively smooth inside wall surface for the vessel and to be able to avoid renewed stenosis, the stents set forth in the opening part of this specification were developed. Those small tubes serve inter alia in conjunction with PCTA to maintain the vessel flow cross-section which is produced by balloon angioplasty in order thereby to ensure long-term success with the PCTA procedure.

The success of such so-called stenting also depends inter alia on how uniformly the stent can come to bear against the wall of the vessel. For, the more uniformly the wall of the vessel is supported, the correspondingly more probable it is that vessel constrictions will not recur in the region of the stent. In that respect a regular stent structure produces a relatively smooth inside surface for the vessel and, with a relatively smooth inside vessel surface, blood particles can only be deposited thereon with difficulty. In addition growths of the intima into the interior of the vessel are prevented to a greater degree by a regular stent structure which covers over the inside surface of the vessel in a relatively closed configuration.

Stents of that kind with a so-called closed structure are also known from the state of the art. By way of example reference may be made here to one of the best-known stents of that kind, the so-called wall stent. That is known for example from U.S. Pat. No. 4,655,771. This stent which has a closed structure is formed from two wires which are regularly knitted in a mesh-like structure and which extend in a spiral configuration on the longitudinal axis of the stent.

The advantage of the closed structure of stents of that kind is however only achieved at the cost of the disadvantage that the stents involve relative longitudinal stiffness during insertion. Those stents do not therefore make it possible in the optimum manner for the stent to be guided through possibly very severely curved vessel portions in the coronary arteries upon insertion in a direction towards the stenosis to be treated. In order to avoid those disadvantages of a closed structure, stents have now been developed which are of a so-called modular nature. In the case of those stents of a modular nature, individual portions which are provided with a closed structure are connected together by flexible connections. Stents of that kind are known for example from U.S. Pat. No. 5,104,404.

A disadvantage with those modular or segmented stents however is that the front edges of the individual modules or segments, which lead in the direction of insertion of the stent, can hook in the inside wall of the vessel. That can give rise to serious complications when inserting a stent. That is particularly problematical more especially insofar as the modular stents—as already referred to above—are used in particular when major curvatures have to be negotiated on the way to the location to be treated. For, it is in such a curve that such a leading edge of a segment becomes particularly easily hooked at the inside surface of the vessel, which is on the outside of the curvature, through which the stent is being passed.

Therefore the object of the invention is to avoid the above-mentioned disadvantages and to provide a stent of the kind set forth in the opening part of this specification which both permits the inside surface of the vessel to be covered in a closed configuration at the location of the stenosis to be treated while at the same time it is sufficiently flexible that it can be displaced to that location.

SUMMARY OF THE INVENTION

In the case of the present invention that object is attained by a stent of the kind set forth in the opening part of this specification, in that the openings provided in the stent have a substantially V-shaped opening area.

The advantages of the invention are in particular that the V-shaped openings, that is to say the V-shaped configuration of the area of the openings, in the tubular structure of the stent, provides a structure which is closed overall so as to provide for good covering of the lesion while at the same time by virtue of the V-shaped openings the flexibility in the longitudinal direction of the stent is increased in comparison with the closed stent structures which are known from the state of the art.

The invention involves the realization that, with V-shaped openings which are arranged in the longitudinal direction of the stent in its tubular portion, in the region of the converging tip of the opening area of the V-shaped openings, there is a region of the material delimiting the opening area, which region is movable in the transverse direction of the stent and which, when the stent is pushed through curves for example in coronary blood vessels permits an adequate degree of flexibility of the stent so that it is easily possible to negotiate such curves.

An advantageous embodiment of the invention is distinguished by first openings of a first size and by second openings of a second size, wherein the second openings are larger than the first openings. In that way, the above-mentioned flexibility of the closed structure is further improved as the small openings can move transversely to an even greater degree within the large openings, in particular if they are engaged into the latter in internested relationship, upon curvature of the stent when it is being pushed through curved coronary blood vessels.

A further preferred embodiment of the invention is distinguished in that first and second openings can occur in alternate succession in the longitudinal direction of the tubular portion of the stent. That provides an optimum compromise between the closed structure and enhanced flexibility of the stent in the transverse direction.

A further preferred embodiment of the present invention is distinguished in that the first and second openings occur in alternate succession in the peripheral direction of the tubular portion of the stent according to the invention. In this embodiment accordingly the advantage already mentioned in regard to the alternate arrangement of the openings in the longitudinal direction is achieved by the alternate arrangement of the openings in the peripheral direction. In this case the advantages of both embodiments can also be combined so that first and second opening sizes occur in alternate succession respectively both in the peripheral and also in the longitudinal direction.

A further advantageous development of the stent according to the invention is distinguished in that the second limbs which form the V of the second opening are longer than the first limbs which form the V of the first openings. In that way the structure according to the invention of the stent can be further loosened up. The alternate arrangement of long and short openings, which is possible with this embodiment, can further enhance the above-mentioned advantages of the stent according to the invention, more specifically, a closed structure with increased flexibility.

In a further advantageous development of the stent according to the invention all openings which occur in succession in the longitudinal direction are disposed with their ends forming the pointed end of the V substantially on a line which also extends longitudinally with respect to the tubular portion. This embodiment therefore advantageously prevents hooking interengagement of the individual boundaries of the openings, which preferably comprise small bar-like elements, when the stent is disposed in a curve. For, because the ends of the V-shaped openings are disposed on a line, they are all at the same spacing relative to the adjacent opening.

A further preferred embodiment of the present invention is distinguished in that all openings which occur in succession in the peripheral direction are disposed with their pointed ends substantially on a line extending in the peripheral direction of the tubular portion of the stent. This also further perfects the advantageous structure described in the preceding paragraph, for avoiding hooking interengagement phenomena when the stent is curved.

A further development of the present invention is distinguished in that the openings have a right limb and a left limb, wherein the right/left limb of the openings terminates at the left/right limb of the respective adjacent openings which are arranged in displaced relationship substantially diagonally in the direction of the right/left limb of the openings. It is advantageously possible in that way to provide for optimum transmission of force between the bar-like elements which advantageously serve as boundaries for the openings, through the structure of the stent. In that respect it is particularly advantageous if the right/left limb of the openings terminates substantially at the center of the left/right limb of the adjacent opening arranged in displaced relationship diagonally in the direction of the right/left limb of the openings. In that way the transmission of force from one opening to the opening which is disposed diagonally therebeside occurs directly onto the center of the limb of the opening so as to provide for optimum application of force to the adjacent openings or the bar-like boundaries thereof.

A further advantageous development of the present invention is distinguished in that the openings are defined by bars and that the bars defining the second openings also define the first openings. It is possible in that way for the tubular portion to be designed in accordance with the invention with the maximum saving of material. In that way, the arrangement achieves the particular advantage that the stent according to the invention can also be used without problem in the region of branchings in the coronary blood vessels. For, by virtue of the very airy and penetrable structure, the stent can also be used for supporting a vessel constriction in the region of a vessel branching without the blood flow from the vessel with the stent into the vessel which is branching off being excessively impeded.

A further preferred embodiment of the invention is distinguished in that the openings are defined by bars, wherein the bars are formed from the remaining material of a tube wall, forming the peripheral surface, of the tubular portion, the material having been removed from that tube wall in the region of the openings, and wherein the bars defining the second openings form the entire material of the tube wall, which remains after the openings have been formed. This embodiment is also advantageously distinguished in that, while being of a closed structure, it nonetheless permits use in the region of vessel branchings with at the same time a high degree of flexibility of the structure overall.

In a development of the invention a further enhancement in flexibility of the stent according to the invention is achieved in that at least one of the ends of the limbs of the V-shaped openings is of a rounded configuration. In that respect, preferably all ends of the V-shape are of a rounded configuration. Those round boundaries, which are preferably formed by the bar-like elements, of the V-shaped openings further improve flexibility and also enhance the reliability of the stent for they avoid peak loadings in the ends of the V-shaped openings. In this connection, it has proven to be particularly advantageous if the individual points or tips of the V-shaped openings are delimited in a rounded configuration by a bar in the form of three-quarters of a circle.

A further increase in the flexibility, as discussed in detail hereinbefore, of the stent according to the invention with at the same time a closed structure can be achieved in that, in an advantageous embodiment, the first openings with the ends of their limbs form slight salients or intrusions in the limbs of the second openings. The boundaries, which in that arrangement are preferably formed by bar-shaped elements, of the openings in the peripheral surface of the stent thus terminate elastically in the diagonally adjacent opening. That elasticity of the diagonal boundaries of the openings also enhances the flexibility of the stent according to the invention for transverse curvature movements.

BRIEF DESCRIPTION OF THE DRAWINGS

Further preferred embodiments of the invention are set forth in the appendant claims.

DETAILED DESCRIPTION OF THE INVENTION

An embodiment by way of example of the present invention will now be described with reference to the single FIGURE.

The FIGURE shows a stent 1 according to the invention. The stent 1 is shown in the FIGURE as a development of the peripheral surface 2 of the stent 1. When the stent 1 is in the condition of being ready for operation, the peripheral surface 2 is joined together with its side 4 which is shown at the bottom in the FIGURE and the side 6 which is shown at the top in the FIGURE so as to afford a tubular portion having the peripheral surface 2.

The peripheral surface 2 has first V-shaped openings 8. Those first V-shaped openings 8 are arranged in mutually juxtaposed relationship in the diagonal direction of the peripheral surface. In this case the V-shaped openings 8 have right limbs 8a which are at the bottom in the FIGURE and left limbs 8b which are at the top in the FIGURE. The limbs 8a and 8b form the V-shape of the V-shaped openings 8. The openings 8 are arranged on the peripheral surface 2 in mutually juxtaposed relationship in such a way that the ends of the limbs 8a and 8b respectively terminate at the center of the adjacent limb 8b and 8a respectively of the opening 8 disposed diagonally therebeside. Thus, the right limb of the opening 8 which is picked out in the drawing, being the limb 8a, terminates at the center of the left limb 8b, which is shown diagonally at the right therebeneath in the drawing, of the opening 8 which is adjacent diagonally to the right therebeneath.

As the above-described diagonal successive arrangement of the V-shaped openings 8 in both diagonals on the peripheral surface 2 shows, the V-shaped openings 8 include between them further but smaller V-shaped openings 10. Such a smaller V-shaped opening 10 is thus surrounded by four larger V-shaped openings 8.

The openings 8 are defined on all sides by webs or bars 12. The bars 12 are the remaining material from the peripheral surface 2, after the material of the peripheral surface 2 was removed at the locations providing the openings 8 and 10. The bars 12 all extend substantially parallel to the diagonals of the peripheral surface 2. In addition, at the locations where the limbs 8a and 8b of the larger openings 8 terminate, that is to say at the points 14 and 16, the bars 12 are each in the form of three-quarters of a circle. That configuration in the shape of three-quarters of a circle is also to be found at the pointed end 18 of the large V-shaped opening 8. In addition the pointed end of the V-shaped opening 10 is also provided with a bar 20 which is rounded off in that way in the configuration of three-quarters of a circle.

The ends 22 and 24 respectively of the right limbs 26 and left limbs 28, with the left limbs 28 being shown at the top in the FIGURE while the right limbs 26 are shown downwardly in the FIGURE, are formed by bars 12 which are in the configuration of three-quarters of a circle. That configuration forming three-quarters of a circle for the bars 12 at the ends 22 and 24 of the limbs 26 and 28 form small bay-like portions or salients which extend into the limbs 8b and 8a respectively of the larger V-shaped openings 8.

What is claimed is:

1. A stent having a longitudinal and a peripheral direction comprising a tubular portion which has a plurality of openings of a first size and a plurality of openings of a second size, the second size being larger than the first size, wherein the first and second openings are of a substantially V-shaped configuration, each having a pointed end and a left and a right limb, wherein each first and second opening has the same longitudinal orientation and alignment in the stent, and wherein the first and the second openings occur in alternate succession in both the longitudinal and peripheral directions of the stent.

2. The stent as set forth in claim 1, wherein the left and right limbs which form the V-shape of each said second opening are longer than the left and right limbs which form the V-shape of each said first opening.

3. The stent of claim 1, wherein each of the first and second openings which occur in succession in the longitudinal direction are disposed with their pointed ends substantially on a line extending longitudinally with respect to the tubular portion.

4. The stent of claim 1, wherein each of the first and second openings which occur in alternate succession in the peripheral direction are disposed with their pointed ends substantially on a line extending in the peripheral direction of the tubular portion.

5. The stent of claim 1, wherein the openings are defined by bars and wherein the bars defining the second openings also define the first openings.

6. The stent of claim 1, wherein the tubular portion has a peripheral surface wherein the plurality of openings are defined by bars, wherein the bars are formed from the remaining material of a tubular wall, forming the peripheral surface of the tubular portion, from which tubular wall the material was removed in the region of the openings, and wherein the bars defining the second openings form the total material of the tubular wall, which remains after formation of the openings.

7. The stent of claim 6 wherein all openings in the peripheral surface are of a V-shaped configuration.

8. The stent of claim 1, wherein each of the second openings has its right limb terminate into the left limbs of the respective adjacent second opening which is arranged in displaced diagonal relationship.

9. The stent of claim 8 wherein each of the second openings has its left limb terminates into the right limb of the respective adjacent second opening which is arranged in displaced diagonal relationship.

10. The stent of claim 9 wherein each said left limb terminates substantially at the center of the right limb.

11. The stent of claim 8 wherein each said right limb terminates substantially at the center of the left limb.

12. The stent of claim 1, wherein each of the right and left limbs of each of the plurality of openings has a first and a second end, with the respective first ends comprising the pointed end.

13. The stent of claim 12 wherein at least one of the ends of the limbs of the openings is of a rounded configuration.

14. The stent of claim 13 wherein the pointed end of the V-shaped openings is of a rounded configuration.

15. The stent of claim 12 wherein the second ends of the limbs of the first openings form slight salients into the limbs of the second openings.

* * * * *